United States Patent
Magni et al.

(10) Patent No.: US 6,638,346 B1
(45) Date of Patent: Oct. 28, 2003

(54) VAPORIZATION INJECTOR

(75) Inventors: Paolo Magni, Besana Brianza Milan (IT); Fausto Munari, Milan (IT); Konrad Grob, Fehraltorf (CH)

(73) Assignee: Thermo Finnigan Italia S.p.A. (IT)

( * ) Notice: Subject to any disclaimer, the term of this patent is extended or adjusted under 35 U.S.C. 154(b) by 0 days.

(21) Appl. No.: 10/110,482

(22) PCT Filed: Oct. 25, 2000

(86) PCT No.: PCT/EP00/10475
§ 371 (c)(1),
(2), (4) Date: Jul. 11, 2002

(87) PCT Pub. No.: WO01/33209
PCT Pub. Date: May 10, 2001

(30) Foreign Application Priority Data

Oct. 29, 1999 (IT) .......................................... MI99A2271

(51) Int. Cl.[7] .............................................. B01D 15/08
(52) U.S. Cl. ............................. 96/105; 73/23.41; 95/87; 95/89
(58) Field of Search ...................... 73/23.41; 95/82–89; 96/101–107

(56) References Cited

U.S. PATENT DOCUMENTS

| | | | | |
|---|---|---|---|---|
| 3,915,677 A | * | 10/1975 | Oppegaard | 55/197 |
| 3,936,374 A | * | 2/1976 | Bradley et al. | 210/656 |
| 4,474,588 A | * | 10/1984 | Hinshaw, Jr. | 96/105 |
| 4,559,063 A | * | 12/1985 | Munari et al. | 95/83 |
| 4,954,149 A | | 9/1990 | Fullemann | 55/386 |
| 5,108,468 A | * | 4/1992 | Ligon, Jr. | 95/86 |
| 5,252,109 A | * | 10/1993 | Munari et al. | 95/87 |
| 5,447,556 A | * | 9/1995 | Pleil et al. | 95/87 |
| 5,607,581 A | * | 3/1997 | Gerner et al. | 210/198.2 |
| 5,686,656 A | | 11/1997 | Amirav et al. | 73/23.41 |
| 5,743,941 A | * | 4/1998 | Gerner et al. | 96/10 |
| 6,042,787 A | * | 3/2000 | Pawliszyn | 422/69 |
| 6,190,613 B1 | * | 2/2001 | Watanabe et al. | 422/99 |
| 6,203,597 B1 | * | 3/2001 | Sasano et al. | 95/87 |
| 6,451,614 B1 | * | 9/2002 | Grob et al. | 436/161 |
| 6,484,560 B1 | * | 11/2002 | Prest | 73/23.41 |

FOREIGN PATENT DOCUMENTS

| | | |
|---|---|---|
| EP | 0 551 847 A | 7/1993 |
| WO | WO 94/28409 A | 12/1994 |

* cited by examiner

*Primary Examiner*—Robert H. Spitzer
(74) *Attorney, Agent, or Firm*—Nixon & Vanderhye PC

(57) ABSTRACT

A vaporization injector for gas chromatography analysis instruments, of the type including a vaporization chamber, heated or which may be heated, with a longitudinally elongated shape, a device for hermetically inserting the needle of a syringe containing the sample (substance to be analysed and solvent) into the chamber, a connection for feeding a carrier gas into the chamber and a gas chromatography capillary column with an upstream end open inside the vaporization chamber. In order to allow the vaporization of large sample volumes, the upstream end of the gas-chromatography column and the injection point of the sample into the vaporization chamber are both arranged adjacent to one of the longitudinal ends of the vaporization chamber and the feed connection for the carrier gas is located adjacent to the other end.

11 Claims, 3 Drawing Sheets

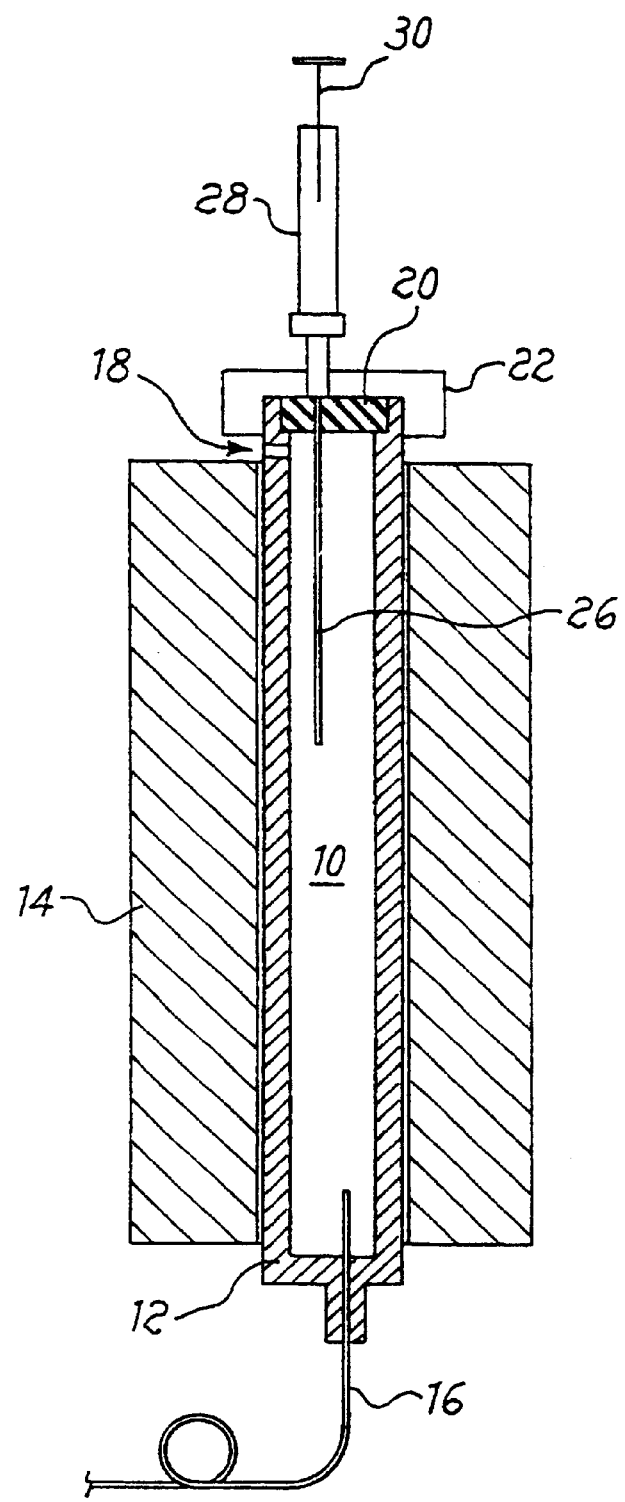

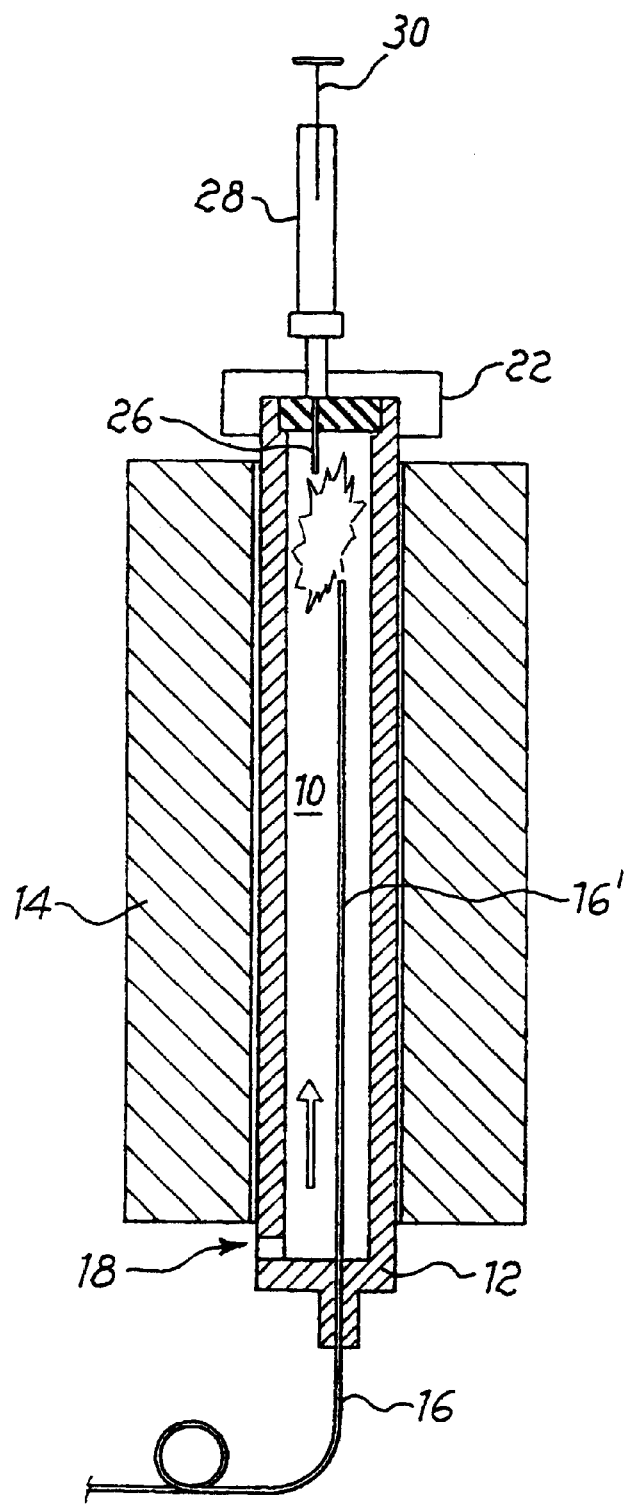

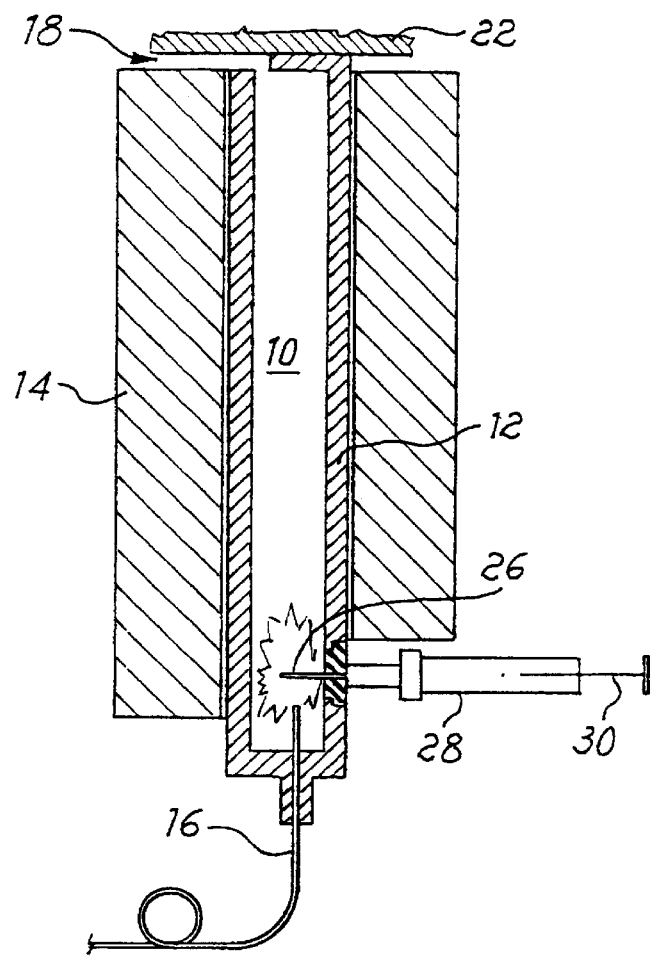
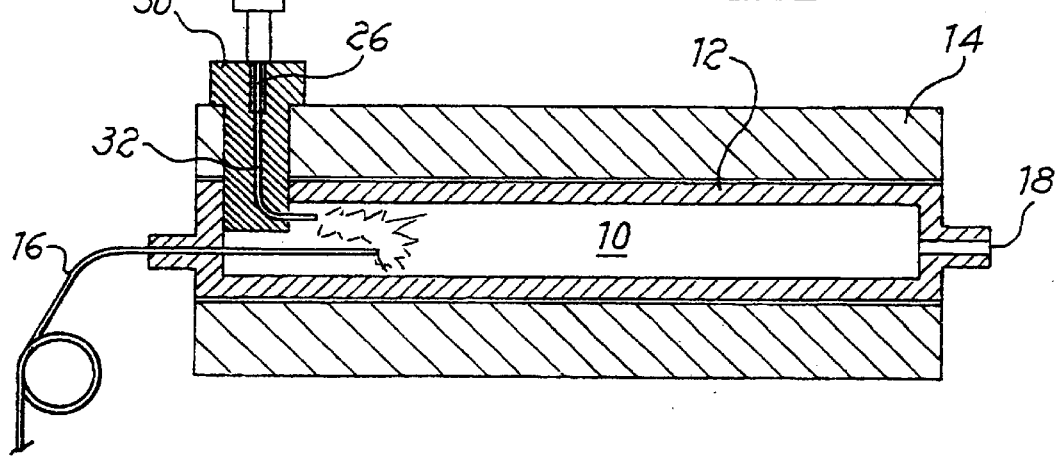

VAPORIZATION INJECTOR

This application is the US national phase of international application PCT/EP00/10475 filed Oct. 25, 2000, which designated the US.

TECHNICAL FIELD

The present invention relates to a vaporization injector in an instrument for gas chromatography analysis.

BACKGROUND ART

Vaporization injectors are well-known in themselves and composed of a so-called vaporization chamber, generally in the form of a heated cylinder, connected on one side (usually the bottom) to a capillary gas chromatography column and closed on the other side (top) by a septum destined to be perforated by a needle for injecting the sample. This needle is fitted to a syringe containing a measured quantity of sample, composed of the substance to be analysed and a solvent for this. The needle is inserted, perforating the septum, to a pre-established position inside the vaporization chamber and the liquid sample is thrust by the syringe piston into this chamber, where it vaporizes before being carried to the gas chromatography column by the carrier gas, which is generally fed in on the same side, namely the top part of the chamber. Depending on the methods chosen, the sample may either be injected into the column partially (split mode) or totally (splitless mode).

In any case, it is important for the sample to vaporize optimally and totally in the vaporization chamber, where it is temporarily stored before being sent to the column. The current trend to increase the sample volumes injected creates some problems, especially in splitless vaporization injection, specifically relevant to the capacity of the vaporization chamber and filling this in an optimum manner. In fact, the transversal dimensions (diameter) of the chamber cannot be increased beyond certain limits for reasons related to vapours mixing with the carrier gas and complete transfer of the sample to the column. On the other hand, an increase in the capacity of the chamber by increasing its length does not have any significant effects, as the vaporized sample tends to be stored in the chamber above the injection point, namely from the tip of the injection needle. Nonetheless, the length of the injection needle is necessarily limited, both for reasons related to mechanical resistance and for reasons concerning excessive dead volume, represented by the internal channel of the needle.

DISCLOSURE OF THE INVENTION

Having stated this, it is now an object of the present invention to provide a vaporization injector, especially of the splitless type, in which the aforesaid limits in the increase of the capacity of the vaporization chamber by means of increasing the longitudinal dimensions of this chamber are overcome and it is thus possible to proportion the vaporization chamber optimally, to obtain temporary storage also of large amounts of sample.

A further object of the invention is to obtain in a reliable manner a cloud of vapour in a specific portion inside the vaporization chamber, contrary to what occurs in the known technique. According to the invention, the aforesaid objects are implemented by means of a vaporization injector as claimed in claim 1.

BEST MODE FOR CARRYING OUT THE INVENTION

The aforesaid and other peculiarities and features of the invention shall now be illustrated in greater detail, with reference to embodiments given merely as an example and schematised in the enclosed drawings in which:

FIG. 1 is a schematic cross-section of a vaporization injector according to the currently known technique;

FIG. 2 is a schematic cross-section of a first embodiment of the invention;

FIG. 3 is a schematic cross-section of a second embodiment of the invention;

FIG. 4 is a schematic representation of a further embodiment of the invention.

With reference firstly to FIG. 1, a conventional vaporizer essentially comprises a generally elongated tubular chamber 10, equipped with a tube of inert material (liner) 12 and heated independently by a device such as a heating element 14. The upstream end of a gas chromatography capillary column 16 is inserted hermetically to the bottom of the chamber 10, whilst a carrier gas feed is represented in the diagram with 18. The top part of the vaporization chamber 10 is closed by a perforable septum 20, held in position by a covering component 22 having a guide for the needle 26 of a syringe 28 with a piston or plunger 30.

The sample, composed of a pre-established quantity of the substance to be analysed and a solvent for this, is drawn up using the syringe 28, the needle of which is then inserted into the guide, perforates the septum 20 and enters the vaporization chamber, where the sample is injected using the piston 30. Operations to draw up the sample and inject it into the vaporization chamber 10 may either be performed manually or using an automatic sampling device. Moreover, penetration of the needle in the chamber 10 is pre-established by a stop, acting for example on the body of the syringe 28.

Inside the chamber 10, at high temperature, the sample vaporizes and is conveyed by the carrier gas, either totally or partially, to the In the embodiment of FIG. 2, according to the invention, the needle 26 of the syringe 28 is preferably much shorter in length than the one of the embodiments of the prior art, for example, of such a length that the tip of the needle, when injecting the sample, only penetrates the vaporization chamber 10 for a length from 0 to 15 mm and with a bottleneck that favours nebulization of the sample injected, according to what is illustrated in another patent application by the same Applicant.

Once more according to the invention, the column 16 has a length 16' that extends along much of the length of the chamber 10, until its open upstream end is in the vicinity or in any case in the zone of the needle tip 26. Nonetheless, column 16' and needle 26 must not be aligned to prevent the risk of liquid parts of the sample from being injected into the column, but they must be in a staggered position. This is achieved, for example, by placing the needle in an eccentric position and/or placing and holding at least the upstream end of the column in an eccentric and staggered position in relation to the position of the needle, by means of a ring in inert material (for example Restek silcosteel) with a seat for the column. Carrier gas supply 18 is instead provided in a position longitudinally opposite the zone with the end of the column 16' and tip of the needle 26, namely in the case illustrated on the bottom of the vaporization chamber 10 and this either permanently or limited to the period in which the sample is injected, by means of a branch on the carrier supply line.

This distribution of components operating inside the vaporization chamber permits implementation of optimum sample vaporization conditions, storage of the sample from the top towards the bottom of the chamber and transfer of the vaporized sample to the gas chromatography column. Moreover, as a result of the conditions of storing the sample in the chamber, there are no limits to the increase in the capacity of the latter by increasing its length, as the length of the needle does not need to be modified. Lastly, the specific layout opposite each other of the points for introducing the sample and carrier gas respectively allows the cloud of vapours created after the sample is injected to be positioned in a reliable and well-defined position inside the vaporization chamber, thus preventing all risks of partial loss of this sample.

The same advantageous operating conditions can be obtained with a layout of the type shown in the diagram of FIG. 3, in which the upstream end of the column 16 and the tip of the needle 26 are arranged not aligned, on the bottom of the vaporization chamber 10, for nebulization and vaporization of the sample in this zone, storage of the vaporized sample towards the top of the chamber 10 and, thereafter, introduction into the gas chromatography column 16 through the carrier gas fed into the chamber 10 from the opposite side, namely from the top, as indicated with 18.

In the embodiment of FIG. 4, the vaporization chamber 10 is arranged horizontally, with the end of the column and the injection point at or adjacent to one end of the chamber 10 and the carrier gas inlet, in 18, at or in the vicinity of the other end. In the injection zone, the chamber has a block 30, for example made of metal, heated either independently or by the atmosphere of the chamber itself, which comprises an inside channel 32 to which the tip of the syringe needle 26 is connected hermetically. The channel in the case illustrated is curved and its end facing the chamber is equipped with one or more bottlenecks to cause nebulization of the injected sample. As specified in a patent application by the same Applicant, this is a means of obtaining optimum sample vaporization, elimination of the septum and washing of the channel 32 by the carrier gas after injection of the sample.

What is claimed is:
1. A vaporization injector for gas chromatography analysis instruments, comprising a vaporization chamber, heated or which may be heated, with a longitudinally elongated shape having an upstream end and a bottom end, a device for hermetically inserting a needle of a syringe containing a sample into the chamber, a connection for feeding a carrier gas into the chamber and a gas chromatography capillary column with an upstream end open inside the vaporization chamber, wherein the upstream end of the gas-chromatography column is in the vicinity of the injection point of the sample into the vaporization chamber and both are positioned adjacent to one of the longitudinal ends of said vaporization chamber and the feed connection for the carrier gas is located in the vicinity of the other end of said vaporization chamber.

2. An injector as claimed in claim 1, characterized in that a limited section of the needle of the syringe penetrates inside the vaporization chamber, for a length from 0 to 15 mm.

3. An injector as claimed in claim 1, wherein the vaporization chamber is vertically elongated, the injection point of the sample is adjacent to the upstream end of the vaporization chamber; the gas-chromatography column crosses the vaporization chamber longitudinally, from the bottom end until its open end is adjacent to the upstream end of such chamber; and in that the carrier gas is introduced in the vicinity of the bottom end of the vaporization chamber.

4. An injector as claimed in claim 3, further comprising means for feeding the carrier gas in the vicinity of the bottom end of the vaporization chamber while the sample is being injected and means for feeding carrier gas in the vicinity of the upstream end of the vaporization chamber during analysis.

5. An injector as claimed in claim 1, wherein the vaporization chamber is vertically elongated, the injection point for injecting the sample is located in the vicinity of the open end of the gas chromatography column and both are positioned to the bottom end of the vaporization chamber; and the feed connection for the carrier gas is located in the vicinity of the upstream end of the vaporization chamber.

6. An injector as claimed in claim 1, wherein the sample is injected into the vaporization chamber in a direction which is not reciprocally aligned with the upstream end of the gas-chromatography column inside the vaporization chamber.

7. An injector as claimed in claim 6, wherein the direction for injecting the sample into the vaporization chamber and an axial direction of the gas chromatography column are parallel to one another and located at one end of the vaporization chamber.

8. An injector as claimed in one of the previous claims, wherein the sample is injected into the vaporization chamber through a channel, fed at its upstream end by the needle of the syringe.

9. An injector as claimed in claim 8, wherein the channel is hermetically coupled to a tip of the needle and a downstream end thereof has one or more bottlenecks for nebulizing the sample injected into the vaporization chamber.

10. An injector as claimed in claim 9, wherein the channel is obtained in a block of material suitable for transmitting heat, heated either independently or by the atmosphere of the vaporization chamber.

11. An injector as claimed in claim 8, wherein the vaporization chamber is arranged essentially horizontal and the channel for introducing the sample is curved, to connect an essentially vertical inlet to an essentially horizontal outlet.

* * * * *